United States Patent [19]

Monroe

[11] Patent Number: 5,096,790

[45] Date of Patent: Mar. 17, 1992

[54] PROCESS OF FORMING HOLOGRAM AND POLYMERIC HOLOGRAPHIC RECORDING MEDIUM WITH SENSITIZER

[75] Inventor: Bruce M. Monroe, Wilmington, Del.

[73] Assignee: E. I. Du Pont de Nemours and Company, Wilmington, Del.

[21] Appl. No.: 552,550

[22] Filed: Jul. 16, 1990

Related U.S. Application Data

[60] Division of Ser. No. 447,721, Dec. 8, 1989, Pat. No. 4,987,230, which is a continuation-in-part of Ser. No. 228,806, Jul. 28, 1988, abandoned.

[51] Int. Cl.⁵ .................... G03H 1/00; G03F 7/020
[52] U.S. Cl. .................................. 430/1; 430/2; 430/4; 430/5; 430/281; 430/290; 522/116; 522/138; 522/120; 359/3; 359/10
[58] Field of Search ............ 430/1, 2, 281, 290, 430/910, 912, 916; 546/94; 522/102, 116, 120, 138, 144, 16, 26; 350/3.6, 3.61, 3.65

[56] References Cited

U.S. PATENT DOCUMENTS

| | | | |
|---|---|---|---|
| 3,658,526 | 4/1972 | Haugu | 430/1 |
| 3,809,732 | 5/1974 | Chandross et al. | 264/22 |
| 3,993,485 | 11/1976 | Chadross et al. | 96/274 |
| 4,173,474 | 4/1979 | Tanaka et al. | 430/1 |
| 4,535,041 | 8/1985 | Fielding et al. | 430/1 |
| 4,588,664 | 5/1986 | Fielding et al. | 430/1 |
| 4,687,720 | 8/1987 | Wreede et al. | 430/2 |
| 4,696,876 | 9/1987 | Cael | 430/1 |
| 4,766,055 | 8/1988 | Kawabata et al. | 430/281 |
| 4,799,746 | 1/1989 | Wreede | 350/3.6 |
| 4,942,102 | 7/1990 | Keys et al. | 430/912 |
| 4,942,112 | 7/1990 | Monroe et al. | 430/282 |
| 4,950,567 | 8/1990 | Keys et al. | 430/1 |
| 4,959,283 | 9/1990 | Smothers et al. | 430/1 |
| 4,959,284 | 9/1990 | Smothers et al. | 430/2 |
| 4,963,471 | 10/1990 | Trout et al. | 430/282 |
| 4,965,152 | 10/1990 | Keys et al. | 430/1 |

OTHER PUBLICATIONS

Wopschall et al., "Dry Photopolymer Film for recording Holograms", Applied Optics, vol. 11, No. 9, Sep. 1972, pp. 2096-2097.

W. C. Hay and B. D. Guenther, "Characterization of Polarois DMP-128 . . .," SPIE vol. 883, Holographic Optics: Design and Applications (1988), pp. 102-105.

R. T. Ingwall and M. Troll, "The Mechanism of Hologram Formation in DMP-128 Photopolymer," SPIE vol. 883, Holographic Optics: Design and Application (1988) pp. 94-101.

*Primary Examiner*—Charles L. Bowers, Jr.
*Assistant Examiner*—Martin J. Angebranndt

[57] ABSTRACT

A new class of sensitizers for photopolymerizable compositions is disclosed derived from cyclic ketones and tricyclic aminoaldehydes. A preferred compound is cyclopentanone, 2.5-bis[(2,3,6,7-tetrahydro-1H, 5H-benzo [i,j]quinolizin-9-yl)methylene]-

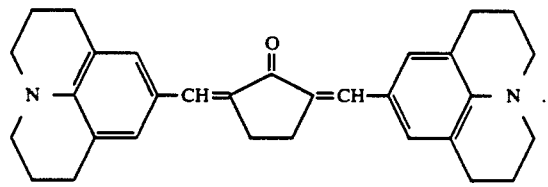

20 Claims, No Drawings

PROCESS OF FORMING HOLOGRAM AND POLYMERIC HOLOGRAPHIC RECORDING MEDIUM WITH SENSITIZER

RELATED APPLICATION

This is a division of application Ser. No. 447,721, filed Dec. 8, 1989, now U.S. Pat. No. 4,987,230, which is a continuation-in-part of Ser. No. 228,806, filed July 28, 1988, now abandoned.

FIELD OF THE INVENTION

This invention relates to new sensitizers for photopolymerizable or photocrosslinkable compositions that absorb in the visible region of the spectrum. More particularly, this invention pertains to photopolymerizable or photocrosslinkable compositions containing photodissociable initiators in combination with selected sensitizers which can be derived from cyclic ketones and certain tricyclic aminoaldehydes.

BACKGROUND OF THE INVENTION

Much work has been done in the field of photopolymerizable compositions to increase the speed of these materials. However, many of the well-known photoinitiators or photoinitiator systems limit the applicability of photopolymerizable compositions because they are activatible primarily by radiation in the ultraviolet region of the spectrum. The availability of reliable, relatively inexpensive lasers which emit in the visible region of the spectrum has made it desirable to develop initiator systems for photopolymerizable materials which are sensitive to visible radiation. Such applications include use of supported photopolymerizable layers for preparing graphic arts films and proofs, printing plates, photoresists, holograms and the like such as are disclosed in U.S. Patents Alles, U.S. Pat. No. 3,458,311; Celeste, U.S. Pat. No. 3,469,982; Chu et al., U.S. Pat. No. 3,649,268; Haugh, U.S. Pat. No. 3,658,526; Chen et al., U.S. Pat. No. 4,323,637; Dueber, U.S. Pat. No. 4,162,162; Bratt et al., U.S. Pat. No. 4,173,673; Cohen et al., U.S. Pat. No. 4,282,308; and Dueber et al., U.S. Pat. No. 4,613,560. In addition these lasers can be used in output devices for electronic imaging systems.

A large number of free-radical generating systems have been utilized as visible sensitizers for photopolymerizable compositions. Redox systems, especially those involving dyes, e.g., Rose Bengal/2-dibutyl-aminoethanol, have been used. Photoreducible dyes and reducing agents such as those disclosed in U.S. Pat. Nos. 2,850,445; 2,875,047; 3,097,096; 3,074,974; 3,097,097; 3,145,104; and 3,579,339; as well as dyes of the phenazine, oxazine, and quinone classes have been used to initiate photopolymerization. A useful discussion of dye sensitized photopolymerization can be found in "Dye Sensitized Photopolymerization" by D. F. Eaton in Adv. in Photochemistry, Vol. 13, D. H. Volman, G. S. Hammond, and K. Gollinick, eds., Wiley-Interscience, New York, 1986, pp. 427-487.

Dueber, U.S. Pat. No. 4,162,162, as well as U.S. Pat. Nos. 4,268,667 and 4,351,893, discloses selected sensitizers derived from aryl ketones and p-dialkylaminoaldehydes. Dueber and Monroe, U.S. Pat. No. 4,565,769 discloses photopolymerizable compositions containing polymeric sensitizers which are activatible by visible radiation.

Baum and Henry, U.S. Pat. No. 3,652,275 discloses selected bis(p-dialkylaminobenzylidene)-ketones as sensitizers to enhance the efficiency of hexaarylbiimidazole initiator systems in photopolymerizable compositions.

The use of visible sensitizers is crucial for the preparation of holograms in photopolymerizable and photocrosslinkable systems such as disclosed in Haugh, U.S. Pat. No. 3,658,526 and Assignees., U.S. patent applications Ser. No. 144,355 filed Jan. 15, 1988, U.S. Pat. No. 4,942,112, Ser. No. 288,916 filed Dec. 29, 1988, U.S. Pat. No. 4,994,347, and Ser. No. 370,274 filed June 22, 1989, U.S. Pat. No. 4,942,102. While suitable sensitizers are available for use in these systems, there is a need for other sensitizers which closely match the spectral laser outputs used, particularly in the regions extending into the yellow, red and infra red portions of the spectrum.

Lasers are also being used to image photopolymerizable resists during the manufacture of printed circuits, optical storage media and the like. While UV and some visible lasers can be used in current systems, there is a need for extended sensitivity photoresists so that high resolution images can be prepared to survive the rigorous processing conditions encountered during manufacture of high quality, printed circuits.

SUMMARY OF THE INVENTION

It is an object of this invention to provide photopolymerizable initiating systems having extended sensitivity in the longer wavelength visible spectral regions. It is a further object of this invention to provide such extended spectral sensitizers that are matched to the spectral output of laser systems used in imaging photopolymerizable or photocrosslinkable materials. It is still a further object of this invention to provide such extended spectral sensitizers for photopolymerizable systems which not only extend the spectral response but also (1) increases both the speed and resolution of the system, (2) improves the thermal stability of the system by increasing the polymerization temperature, and (3) improves the processing characteristics of the resulting resist image.

These objects and others are satisfied by the novel sensitizers of this invention which are compounds having the following structure:

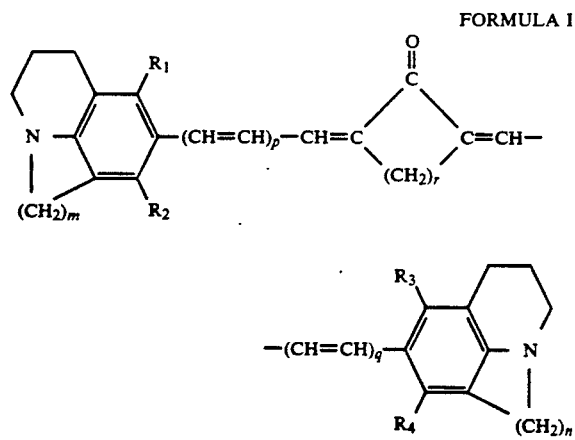

FORMULA I wherein p and q independently are 0 or 1 and r, m and n independently are 2 or 3; and $R_1$, $R_2$, $R_3$ and $R_4$, independently are selected from the group consisting of hydrogen and alkyl having 1 to 4 carbon atoms or alkoxy having 1 to 4 carbon atoms.

Another aspect of this invention relates to an improved photohardenable composition having extended spectral response containing:

(1) an ethylenically unsaturated compound capable of free radical generated addition polymerization, and (2) a free radical generating initiation system activated by actinic radiation, and (3) an extended spectral sensitizer having the structure of Formula I.

An additional aspect of this invention relates to an improved supported dry film photoresist layer wherein the photoresist contains:

(1) an ethylenically unsaturated compound capable of free radical generated addition polymerization, (2) a free radical generating initiation system activated by actinic radiation, and (3) a polymeric material, and (4) an extended spectral sensitizer having the structure of Formula I.

DETAILED DESCRIPTION OF THE INVENTION

Photohardenable Compositions

The novel compositions of this invention are useful in sensitizing photohardenable systems which are initiated by free radicals generated by actinic radiation. Typically, photohardening proceeds by free radical initiated addition polymerization and/or crosslinking of ethylenically unsaturated monomeric compounds. While the photohardenable systems contain the requisite photoinitiating and monomeric compounds along with the sensitizers of this invention, the formulation may contain other constituents for a specific use. Such constituents include stabilizers, adhesion and coating agents, and the like. Photohardenable systems wherein the compounds of this invention are particularly useful are holographic photopolymer materials and photoresist materials such as a liquid or dry film.

Sensitizers

The novel compositions of this invention have the general structure:

FORMULA I

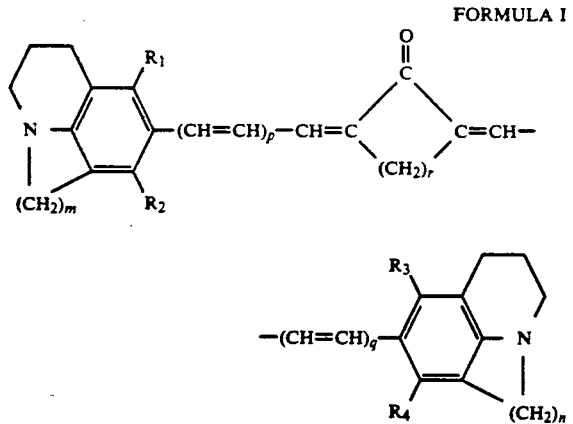

wherein p and q independently are 0 or 1 and r, m and n independently are 2 or 3; and $R_1$, $R_2$, $R_3$ and $R_4$, independently are selected from the group consisting of hydrogen and alkyl having 1 to 4 carbon atoms or alkoxy having 1 to 4 carbon atoms.

In a preferred embodiment of the present invention at least one of the following conditions is present: p and q are identical, m and n are identical, $R_1$ and $R_2$ are identical and $R_3$ and $R_4$ are identical. In a more preferred embodiment the following are identical: p and m and n; and $R_1$, $R_2$, $R_3$ and $R_4$. A preferred definition for $R_1$, $R_2$, $R_3$ and $R_4$ is hydrogen. A preferred integer for m and n is 3. A preferred integer for p and q is 0 and a preferred integer for r is 2. A particularly preferred sensitizer of this invention is JAW, i. e. cyclopentanone, 2,5-bis[(2,3,6,7-tetrahydro-1H,5H-benzo[i,j]quinolizin-9-yl)methylene]-, in which p and q are 0, m and n are 3, r is 2, and $R_1$, $R_2$, $R_3$, and $R_4$ are each hydrogen.

The sensitizers of this invention may be used individually or in combination with members of the same class of compositions or with other sensitizing compositions such as those disclosed in U.S. Pat. No. 3,652,275; U.S. Pat. No. 4,162,162; U.S. Pat. No. 4,268,667; U.S. Pat. No. 4,351,893; U.S. Pat. No. 4,535,052; U.S. Pat. No. 4,565,769 and the like. The use of two or more such compositions effects sensitization over a broader spectral range to match a variety of laser output radiation.

Initiator Systems

A large number of free-radical generating compounds can be utilized in the practice of this invention. Preferred initiator systems are 2,4,5-triphenylimidazolyl dimers with hydrogen donors, also known as the 2,2',4,4',5,5'-hexaaryl-biimidazoles or HABI's, and mixtures thereof, which dissociate on exposure to actinic radiation to form the corresponding triarylimidazolyl free radicals. These hexaarylbiimidazoles absorb maximally in the 255-275 nm region of the spectrum, and usually show some, though lesser absorption in the 300-375 nm region. Although the absorption bands tend to tail out to include wavelengths as high as 430 nm, these compounds normally require light rich in the 255-375 nm region of the spectrum for their dissociation.

HABI's and use of HABI-initiated photopolymerizable systems have been previously disclosed in a number of patents. These include Chambers, U.S. Pat. No. 3,479,185, Chang et al., U.S. Pat. No. 3,549,367, Baum and Henry, U.S. Pat. No. 3,652,275, Cescon, U.S. Pat. No. 3,784,557, Deuber, U.S. Pat. No. 4,162,162, Dessauer, U.S. Pat. No. 4,252,887, Chambers et al., U.S. Pat. No. 4,264,708, and Tanaka et al., U.S. Pat. No. 4,459,349, the disclosures of which are incorporated herein by reference. Useful 2,4,5-triarylimidazolyl dimers are disclosed in Baum and Henry, U.S. Pat. No. 3,652,275 column 5, line 44 to column 7, line 16, the disclosure of which is incorporated herein by reference.

Preferred HABI's are 2-o-chlorosubstituted hexaphenylbiimidazoles in which the other positions on the phenyl radicals are unsubstituted or substituted with chloro, methyl or methoxy. The most preferred initiators include CDM-HABI, i.e., 2-(o-chlorophenyl)-4,5-bis(m-methoxyphenyl)-imidazole dimer; o-Cl-HABI, i.e., 1,1'biimidazole, 2,2'-bis (o-chlorophenyl)-4,4',5,5'-tetraphenyl-; and TCTM-HABI, i.e., 1H-imidazole, 2,5-bis(o-chlorophenyl)-4-[3,4-dimethoxyphenyl]-, dimer, each of which is typically used with a hydrogen donor.

Processes for producing HABI compounds result in a mixture of isomers and other impurities. Use of high concentrations of these impure materials can provide photopolymerizable compositions with high sensitivity but poor shelf-life or storage stability due to crystallization. It has been found that purification of the materials by various methods can provide relatively pure materials which can be used in high concentration without crystallization.

The HABI's can be purified sufficiently for use in this invention by merely dissolving them in methylene chloride, filtering and recrystallizing by adding methanol or ether. If desired, the solution of the HABI in methylene chloride can be eluted through a silica gel column prior to recrystallization.

Chain Transfer Agents

Conventional chain transfer agents, or hydrogen donors, identified in the prior art can be used herein such as for use with HABI-initiated photopolymerizable systems can be used. For example, Baum and Henry, U.S. Pat. No. 3,652,275 lists N-phenylglycine, 1,1-dimethyl-3,5-diketocyclohexane, and organic thiols such as 2-mercaptobenzothiazole, 2-mercaptobenzoxazole, 2-mercaptobenzimidazole, pentaerythritol tetrakis(mercaptoacetate), 4-acetamidothiophenol, mercaptosuccinic acid, dodecanethiol, and betamercaptoethanol. Others which can be used include various tertiary amines known in the art, 2-mercaptoethane sulfonic acid, 1-phenyl-4H-tetrazole-5-thiol, 6-mercaptopurine monohydrate, bis-(5-mercapto-1,3,4-thiodiazol-2-yl, 2-mercapto-5-nitrobenzimidazole, and 2-mercapto-4-sulfo-6-chlorobenzoxazole. Other hydrogen donor compounds useful as chain transfer agents in photopolymer compositions include various other types of compounds, e.g., (a) ethers, (b) esters, (c) alcohols, (d) compounds containing allylic or benzylic hydrogen, e.g., cumene, (e) acetals, (f) aldehydes, and (g) amides, as disclosed in column 12, lines 18 to 58, of MacLachlan, U.S. Pat. No. 3,390,996, incorporated herein by reference.

For photopolymerizable compositions which contain the monomer N-vinyl carbazole, the preferred chain transfer agents are: 5-chloro-2-mercaptobenzothiazole; 2-mercaptobenzothiazole; 1-H-1,2,4-triazole-3-thiol; 6-ethoxy-2-mercaptobenzothiazole; 4-methyl-4H-1,2,4-triazole-3-thiol; and 1-dodecanethiol. Except for systems which contain the monomer N-vinyl carbazole, the preferred chain transfer agents are 2-mercaptobenzoxazole (2-MBO) and 2-mercaptobenzthiazole (2-MBT).

Although the sensitizing compositions are preferably used with the HABI initiating systems described above, they are also useful with many other initiating systems. Typical free radical-generating addition polymerization initiators activatable by actinic light and thermally inactive below 185° C. include the substituted or unsubstituted polynuclear quinones which are compounds having two intracyclic carbon atoms in a conjugated carbocyclic ring system, e.g., 9,10-anthraquinone, 1-chloroanthraquinone, 2-chloro-anthra-quinone, 2-methylanthraquinone, 2-ethyl-anthraquinone, 2-tert-butylanthraquinone, octamethylanthraquinone, 1,4-naphthoquinone, 9,10-phenanthrenequinone, 1,2-benzanthraquinone, 2,3-benzanthraquinone, 2-methyl-1,4-naphthoquinone, 2,3-dichloronaphthoquinone, 1,4-dimethylanthraquinone, 2,3-dimethylanthraquinone, 2-phenylanthraquinone, 2-3-diphenylanthraquinone, sodium salt of anthraquinone alpha-sulfonic acid, 3-chloro-2-methylanthraquinone, retenequinone, 7,8,9,10-tetrahydronaphthacenequinone, and 1,2,3,4-tetrahydrobenz(a)anthracene-7,12-dione. Other photoinitiators which are also useful, even though some may be thermally active at temperatures as low as 85° C., are described in U.S. Pat. No. 2,760,863 and include vicinal ketaldonyl alcohols, such as benzoin, pivaloin, acyloin ethers, e.g., benzoin methyl and ethyl ethers; alpha-hydrocarbon-substituted aromatic acyloins, including alpha-methylbenzoin, alpha-allylbenzoin and alpha-phenylbenzoin. Photoreducible dyes and reducing agents disclosed in U.S. Pat. Nos.: 2,850,445; 2,875,047; 3,097,096; 3,074,974; 3,097,097; and 3,145,104 as well as dyes of the phenazine, oxazine, and quinone classes; Michler's ketone, benzophenone, dialkylamino benzaldehyde, benzaldehyde, dialkylamino benzoate esters, and combinations thereof as disclosed in Barzynski et al., U.S. Pat. No. 4,113,593. Also useful as initiators are the cyclohexadienones disclosed in U.S. 4,341,860 as well as the combination with 1,2-dibromoethanes disclosed in U.S. Pat. No. 4,634,657.

Monomers

Contemplated monomers include those which form both water-soluble and water-insoluble polymers. Typical monomers are alkylene or polyalkylene glycol diacrylate prepared from an alkylene glycol of 2 to 15 carbons or a polyakylene ether glycol of 1 to 10 ether linkages, and those disclosed in Martin and Barney, U.S. Pat. No. 2,927,022, e.g., those having a plurality of addition polymerizable ethylenic linkages, particularly when present as terminal linkages, and especially those wherein at least one and preferably most of such linkages are conjuqated with a doubly bonded carbon, including carbon doubly bonded to carbon and to such heteroatoms as nitrogen, oxygen and sulfur. Outstanding are such materials wherein the ethylenically unsaturated groups, especially the vinylidene groups, are conjugated with ester or amide structures.

The following specific compounds are illustrative of this class: unsaturated esters of alcohols, preferably polyols and particularly such of the alpha-methylene carboxylic acids, e.g., ethylene glycol diacrylate, diethylene glycol diacrylate, glycerol diacrylate, glycerol triacrylate, ethylene glycol dimethacrylate, 1,3 propanediol dimethacrylate, 1,2,4-butanetriol trimethacrylate, 1,4-cyclohexanediol diacrylate, 1,4-benzenediol dimethacrylate, pentaerythritol tetramethacrylate, 1,3-propanediol diacrylate, 1,3-pentanediol dimethacrylate, the bis-acrylates and methacrylates of polyethylene glycols of molecular weight 200–500, and the like; unsaturated amides, particularly those of the alphamethylene carboxylic acids, and especially those of alpha-omega-diamines and oxygen-interrupted omega-diamines, such as methylene bis-acrylamide, methylene bis-methacrylamide, methylene bis-methacrylamide, 1,6-hexamethylene bis-acrylamide, diethylene triamine tris-methacrylamide, bis(gamma-methacrylamidopropoxy) ethane beta-methacrylamidoethyl methacrylate, N-(beta-hydroxyethyl)-beta-(methacrylamido) ethyl acrylate and N,N-bis(beta-methacrylamido) ethyl acrylate and N,N-bis(beta-methacryloxyethyl) acrylamide; vinyl esters such as divinyl succinate, divinyl adipate, divinyl phthalate, divinyl terephthalate, divinyl benzene-1,3-disulfonate, and divinyl butane-1,4-disulfonate, styrene and derivatives thereof and unsaturated aldehydes, such as sorbaldehyde (hexadienal).

An outstanding class of these preferred addition polymerizable components are the esters and amides of alpha-methylene carboxylic acids and substituted carboxylic acids with polyols and polyamines wherein the molecular chain between the hydroxyls and amino groups is solely carbon or oxygen-interrupted carbon. The preferred monomeric compounds are polyfunctional, but monofunctional monomers can also be used. In addition, the polymerizable, ethylenically unsaturated polymers of Burg U.S. Pat. No. 3,043,805, Martin U.S. Pat. No. 2,929,710 and similar materials may be used alone or mixed with other materials. Acrylic and methacrylic esters of polyhydroxy compounds such as pentaerythritol and trimethylolpropane, and acrylic and methacrylic esters of adducts of ethylene oxide and polyhydroxy compounds such as those described in Cohen and Schoenthaler, U.S. Pat. No. 3,380,831 are also useful. The photocrosslinkable polymers disclosed in Schoenthaler, U.S. Pat. No. 3,448,295 and Celeste, U.S. Pat. No. 3,448,089, may also be used. The amount of monomer added varies with the particular polymer used. Other useful ethylenically unsaturated compounds are the ethylenically unsaturated diester polyhydroxy polyethers described in U.S. Pat. Nos. 3,661,576, 3,373,075 and 3,637,618.

Binders

For the purpose of this invention a binder is a preformed macromolecular polymeric or resin material typically having a molecular weight above 1000. Suitable binders include the following: polymers and copolymers of acrylate and alpha-alkyl acrylate esters, e.g., polymethyl methacrylate and polyethyl methacrylate; polymers and copolymers of vinyl esters and their hydrolysis and partial hydrolysis products, e.g., polyvinyl acetate, polyvinyl acetate/acrylate, polyvinyl acetate/methacrylate and hydrolyzed polyvinyl acetate; ethylene/vinyl acetate copolymers; styrene polymers and copolymers, with, e.g., maleic anhydride, or acrylate and methacrylate esters; vinylidene chloride copolymers, e.g., vinylidene chloride/acrylonitrile, vinylidene chloride/methacrylate, and vinylidene chloride/vinyl acetate; vinyl chloride polymers and copolymers, e.g., vinyl chloride/acetate; saturated and unsaturated polyurethanes; synthetic rubbers, e.g., butadiene/acrylonitrile, acrylonitrile/butadiene/styrene, methacrylate/acrylonitrile/butadiene/styrene copolymers, 2-chlorobutadiene-1,3 polymers, chlorinated rubber, and styrene/butadiene/styrene and styrene/isoprene/styrene block copolymers; polyepoxides having average molecular weights from about 4,000 to 1,000,000; copolyesters, e.g., those prepared from the reaction product of a polymethylene glycol of the formula HO(CH$_2$O)$_n$OH, where n is an integer of from 2 to 10 inclusive, with (1) hexahydroterephthalic, sebacic and terephthalic acids, (2) terephthalic, isophthalic and sebacic acids, (3) terephthalic and sebacic acids, (4) terephthalic and isophthalic acids, or (5) mixtures of copolyesters prepared from said glycols and (i) terephthalic, isophthalic and sebacic acids and (ii) terephthalic, isophthalic, sebacic and adipic acids; nylons or polyamides, e.g., N-methoxymethyl polyhexamethylene adipamide; cellulose esters, e.g., cellulose acetate, cellulose acetate succinate and cellulose acetate butyrate; cellulose ethers, e.g., methyl cellulose, ethyl cellulose and benzyl cellulose; polycarbonates; polyvinyl acetals, e.g., polyvinyl butyral, polyvinyl formal; and polyformaldehydes. Suitable binders for use in the photopolymerizable compositions of this invention also include those disclosed in Fryd et al., U.S. Pat. No. 4,726,877; Kempf, U.S. Pat. No. 4,716,093; Briney et al., U.S. Pat. No. 4,517,281; Leberzammer et al., U.S. Pat. No. 4,353,978; Chen et al., U.S. Pat. No. 4,323,637; Flint et al., U.S. Pat. No. 4,293,635; Cohen et al., U.S. Pat. No. 4,282,308; Gervay et al., U.S. Pat. No. 4,278,752; Celeste, U.S. Pat. No. 3,770,438; Haugh, U.S. Pat. No. 3,658,526; Chu et al., U.S. Pat. No. 3,649,268 and Celeste, U.S. Pat. No. 3,469,982.

In the stable, solid, photopolymerizable compositions adapted for the preparation of holograms the monomer is a non-gaseous ethylenically unsaturated component capable of addition polymerization. In the preferred composition the binder and the monomer are selected so that either the binder or the monomer contains one or more moieties selected from the group consisting of substituted or unsubstituted phenyl, phenoxy, naphthyl, naphthyloxy, and heteroaromatic groups containing up to three aromatic rings; chlorine; and bromine, and the other constituent is substantially free of the specified moieties. Compositions of this type are disclosed in Assignees U.S. patent applications Ser. No. 144,281, filed Jan. 5, 1988; abandoned and Ser. No. 144,355, filed Jan. 15, 1988, U.S. Pat. No. 4,942,112; and Ser. No. 144,840, filed Jan. 15, 1988, abandoned; which are incorporated herein by reference.

Other Components

A wide range of nonpolymerizable plasticizers are effective in achieving improved exposure and development temperature latitude. When a macromolecular binder is present in the layer, plasticizer would be selected which is compatible with the binder as well as the ethylenically unsaturated monomer and other components of the composition. With acrylic binders, for example, plasticizers can include dibutyl phthalate and other esters of aromatic acids; esters of aliphatic polyacids such as diisooctyl adipate, and nitrate esters; aromatic or aliphatic acid esters of glycols, polyoxyalkylene glycols, aliphatic polyols; alkyl and aryl phosphates; low molecular weight polyesters of poly-alpha-methylstyrenes; chlorinated paraffins; and sulfonamide types can be used. In general, water insoluble plasticizers are preferred for greater high humidity storage stability, but are not necessary to get improved latitude.

Many ethylenically unsaturated monomers are subject to thermal polymerization, especially when stored for long periods or at elevated temperatures. When such compounds are supplied commercially, it is customary for them to contain a small amount of a thermal polymerization inhibitor. These inhibitors can be left in the monomers when the photopolymerizable compositions of this invention are prepared, as in the Examples which follow. The resulting compositions usually have satisfactory thermal stability. If unusual thermal exposure is anticipated, or if monomers containing little or no thermal polymerization inhibitor are employed, compositions with adequate shelf life can be obtained by incorporating, at about 1 to 500 ppm by weight of monomer, of a thermal polymerization inhibitor. Useful thermal stabilizers include: hydroquinone, phenidone, p-methoxyphenol, alkyl- and aryl-substituted hydroquinones and quinones, tert-butyl catechol, pyrogallol, copper resinate, naphthylamines, beta-naphthol, cuprous chloride, 2,6-di-tert-butyl p-cresol, phenothiazine, pyridine, nitrobenzene, dinitrobenzene, p-toluquinone and chloranil. The dinitroso dimers described in Pazos, U.S. Pat. No. 4,168,982 are also useful. A preferred reversible thermal stabilizer is TAOBN, i.e., 1,4,4-trimethyl-2,3-diazobicyclo(3.2.2)-non-2-ene-2,3-dioxide.

By the incorporation of optical brightening agents into the photopolymerizable layer, the image record is produced substantively free from distortion due to halation effects. Suitable optical brighteners useful in the process of the invention include those disclosed in, U.S. Pat. Nos. 2,784,183; 3,664,394; and 3,854,950. Specific optical brighteners which are particularly useful in the photopolymerizable elements of this invention are 2-(stibyl-4")-(naphto-1',2',4,5)-1,2,3-triazol-2"-sulfonic acid phenyl ester and 7-(4'chloro-6,-diethylamino-1',3',5,-triazine-4'-yl)amino-3-phenyl coumarin. Ultraviolet radiation absorbing materials useful in the invention are also disclosed in U.S. Pat. No. 3,854,950.

Compounds which have been found useful as release agents may also be incorporated in film compositions such as described in Bauer, U.S. Pat. No. 4,326,010. A preferred release agent is polycaprolactone.

Other inert additives can be employed such as dyes, pigments and fillers. These additives are generally present in minor amounts so as not to interfere with the exposure of the photopolymerizable layer.

Substrates/Coating/Exposure

The photopolymerizable compositions can be coated onto a wide variety of substrates. By "substrate" is meant any natural or synthetic support, preferable one which is capable of existing in a flexible or rigid form. For example, the substrate can be a metal sheet or foil, a sheet or film of synthetic organic resin, cellulose paper, fiberboard, and the like, or a composite of two or more of these materials.

The particular substrate will generally be determined by the intended application. For example, when printed circuits are produced, the substrate may be a plate which is a copper coating on fiberboard; in the preparation of lithographic printing plates, the substrate may be anodized aluminum. Specific substrates include alumina-blasted aluminum, anodized aluminum, alumina-blasted polyethylene terephthalate film, polyethylene terephthalate film, e.g., resin-subbed polyethylene terephthalate film, polyvinyl alcohol-coated paper, crosslinked polyester-coated paper, nylon, polycarbonate, glass, cellulose acetate film, heavy paper such as lithographic paper, and the like.

Any convenient source or sources of actinic radiation providing wavelengths in the region of the spectrum that overlap the absorption bands of the photosensitizer can be used to activate the steps of photopolymerization or inhibitor formation as disclosed in U.S. Pat. No. 4,162,162. The radiation can be natural or artificial, monochromatic or polychromatic, incoherent or coherent, and for high efficiency should correspond closely in wavelengths to those of the initiator system or photoinhibitor compound.

Conventional light sources include fluorescent lamps, mercury, metal additive and arc lamps providing narrow or broad light bands centered near 405, 436 and 546 nm. Coherent light sources are xenon, argon ion, and ionized neon lasers, as well as tunable dye lasers and the frequency doubled neodymium:YAG laser, whose emissions fall within or overlap the visible absorption bands of the sensitizer. For the exposure of holographic photopolymer systems coherent light sources, i.e., lasers, which emit in the visible are preferred. Particularly preferred are the argon ion laser, the krypton-ion laser, and the frequency doubled neodymium:YAG laser.

When broad spectrum light sources are used to form an image from negative separation transparencies in a two exposure system using a nitroaromatic photoinhibitor compound, it is generally necessary to filter out the radiation in the spectral range above 400 nm during the initial, imagewise exposure. A filter capable of transmitting radiation in the spectral range of 315 to 380 nm and absorbing radiation in the spectral range 400 to 550 is described is Looney, U.S. Pat. No. 4,167,490. Such positive working processes are described in Pazos U.S. Pat. No. 4,198,242, Dueber U.S. Pat. No. 4,162,162, and Dueber and Nebe U.S. Pat. No. 4,477,556.

Holographic Recording

The term "image recording" is conventionally taken to mean a process which produces a spatial pattern of optical absorption in the recording medium. Photographic processes are well known examples of this type of process.

In a broader sense, however, the word "image" means a spatial variation of the optical properties of a sample in such a way as to cause a desired modification of a beam of light passing through, or reflecting from, the sample. Refractive index images in general and holograms in particular, which modulate the phase, rather than the amplitude, of the beam passing through them are usually referred to as phase holograms. Phase holographic image recording systems produce a spatial pattern of varying refractive index rather than optical absorption in the recording medium and, thus, can modulate without absorbing it. This type of refractive index image formation also includes a number of optical elements or devices, such as holographic lenses, gratings, mirrors, and optical waveguides, which superficially bear little resemblance to absorption images.

Holography is a form of optical information storage. The general principles are described in a number of references, e.g., "Photography by Laser" by E. N. Leith and J. Upatnieks in *Scientific American*, 212, No. 6,24–35 (June, 1965). A useful discussion of holography is presented in "Holography", by C. C. Guest, in *Encyclopedia of Physical Science and Technology*, Vol 6, pp. 507–519, R. A. Meyers, Ed., Academic Press, Orlando, Fla., 1987. In brief, the object to be photographed or imaged is illuminated with coherent light (e.g., from a laser) and a light sensitive recording medium (e.g., a photographic plate) is positioned so as to receive light reflected from the object. This beam of reflected light is known as the object beam. At the same time, a portion of the coherent light is directed to the recording medium, bypassing the object. This beam is known as the reference beam. The interference pattern that results from the interaction of the reference beam and the object beam impinging on the recording medium is recorded in the recording medium. When the processed recording medium is subsequently appropriately illuminated and observed at the appropriate angle, the light from the illuminating source is diffracted by the hologram to reconstruct the wavefront that originally reached the recording medium from the object. Thus, the hologram resembles a window through which the virtual image of the object is observed in full three-dimensional form, complete with parallax.

Holograms that are formed by allowing the reference and object beams to enter the recording medium from the same side are known as transmission holograms. Interaction of the object and reference beams in the recording medium forms fringes of material with varying refractive indices which are approximately normal to the plane of the recording medium. When the hologram is played back by viewing with transmitted light, these fringes refract the light to produce the viewed virtual image. Such transmission holograms may be produced by methods which are well known in the art, such as disclosed in Leith and Upatnieks, U.S. Pat. Nos. 3,506,327; 3,838,903 and 3,894,787.

Holograms formed by allowing the reference and object beams to enter the recording medium from opposite sides, so that they are traveling in approximately opposite directions, are known as reflection holograms. Interaction of the object and reference beams in the recording medium forms fringes of material with varying refractive indices which are, approximately, planes parallel to the plane of the recording medium. When the hologram is played back these fringes act as partial mirrors reflecting incident light back to the viewer. Hence, the hologram is viewed in reflection rather than in transmission.

Reflection holograms may be produced by an on-axis method wherein the beam of coherent radiation is projected through the recording medium onto an object therebehind. In this instance, the reflected object beam returns and intersects with the projected beam in the plane of the recording medium to form fringes substantially parallel to the plane of the medium. Reflection holograms also may be produced by an off-axis method wherein a reference beam is projected on one side of the recording medium and an object beam is projected on the reverse side of the medium. In this instance the object beam is formed by illuminating the object with coherent radiation which has not passed through the recording medium. Rather, the original beam of coherent radiation is split into two other portions, one portion being projected on the medium and the other portion being manipulated to project on the object behind the medium. Reflection holograms produced by an off-axis process are disclosed in U.S. Pat. No. 3,532,406.

A holographic mirror is the simplest possible reflection hologram. It can be created by splitting a single laser beam and recombining the beams at the recording medium, or the unsplit laser beam can be projected through the medium onto a plane mirror therebehind. A set of uniformly spaced fringes with a sinusoidal-like intensity distribution is formed which are oriented parallel to the bisector of the obtuse angle between the two beams propagating in the recording medium. If the obtuse angle is 180° and the beams are normal to the plane of the medium, the fringes will be parallel to the plane of the medium. If the two beams do not make equal angles with the normal to the plane of the medium, then the fringes which are formed will be slated at an acute angle relative to the plane of the medium. The holographic mirror can be characterized by its wavelength of maximum reflection and by its reflection efficiency, that is the percent of incident radiation which is reflected at its wavelength of maximum reflection.

Industrial Applicability

The photopolymerizable compositions of this invention may possess very little residual color and good solubility and shelf life; they are useful in printing plates for offset and letter press, engineering drafting films, as well as photoresists in liquid or dry film form for making printed circuits or in chemical milling or as solder masks. Other specific uses will be evident to those skilled in the art.

In photoresist applications, thin film resists prepared from the compositions of this invention are useful for the preparation of microcircuits. The resist can be either organic solvent developable or aqueous developable.

Photoresists are temporary protective coatings which allow selected modification of uncovered underlying substrate surfaces, areas, e.g., by etching or plating, while protecting covered surface areas from such modification. Once modification is complete the photoresist typically is removed. Solder masks are permanent protective coatings which are selectively applied to portions of a printed circuit board to confine solder to pad areas on the board and to prevent bridging between conductors during tinning operations and during soldering of components. A solder mask also functions to prevent or minimize corrosion of the base copper conductors and as a dielectric to insulate certain components in adjacent circuitry.

In addition to improved spectral sensitivity, photoresist compositions containing a sensitizer of this invention also show improved speed, and the resultant resist images show improved resolution and processing characteristics. The improvement in both speed and resolution is unexpected since an increase in speed normally leads to a loss of resolution. The improved processing characteristics allow gold to be plated on top of copper without the formation of defects due to loss of resist during plating.

Photopolymerizable compositions containing the sensitizers of this invention show good visible light sensitization. The broad sensitization range coupled with the effectiveness of the sensitization enables polymeric images to be formed. The polymeric images formed may be further processed by development to produce resist images or other such relief images described above or the polymeric image formed may be a refractive image type formed without removal to produce a transmission or reflection hologram or the like.

Compared to photopolymerizable compositions containing prior sensitizers, those which contain a sensitizer of this invention show unexpected increases in the thermal stability. This improved thermal stability, which is indicated by their increased polymerization temperatures, allows these compositions to be dried at higher temperatures during the coating and drying steps of manufacture. Higher drying temperatures produce faster drying and a resulting increase in rate of manufacture. In addition, these compositions will have longer shelf lives due to enhanced thermal stability.

Synthesis

The sensitizers of this invention are readily prepared by condensation of the corresponding aldehydes with cyclic ketones. The condensation is readily carried out with basic catalysts as described in Example 1.

A single step procedure for the synthesis of julolidine and substituted julolidines from aniline and from substituted anilines, respectively, is disclosed in "Synthesis of Julolidines from Anilines", H. Katayama, E. Abe, and K. Kaneko, *J. Heterocyclic Chem.*, 19, 925–6, 1982. In brief, aniline or a m- or p-substituted aniline is refluxed with 1,3-bromochloropropane in the presence of sodium carbonate. The water thus formed is removed by filtering the condensate from the reflux condenser through molecular sieves. The crude julolidines are purified as hydrobromide salts. An additional example of the synthesis of a substituted julolidine by this procedure is given in "Chemiluminescence of Organic Peroxides: Intramolecular Electron-Exchange Luminescence from a Secondary Perester", J. Van Gompel and G. B. Schuster, *J. Org. Chem.*, 52, 1465–8, 1987.

Julolidines can be formulated to their corresponding aldehydes by various methods for the formulation of aromatic compounds well know to those skilled in the art. As an example of the formulation of a julolidine, the formulation of julolidine to its aldehyde is described in Example 2. An example of the formulation of a substituted julolidine to its corresponding aldehyde using phosphorus oxychloride in N,N-dimethyl formamide is described in "Chemiluminescence of Organic Peroxides: Intramolecular Electron-Exchange Luminescence from a Secondary Perester", J. Van Gompel and G. B. Schuster, *J. Org. Chem.*, 52, 1465–8, 1987.

6-Lilolidine carboxaldehyde (4H-pyrrolo[3,2,1-i,j]quinoline-6-carboxaldehyde, 1,2,5,6-tetrahydro-), the [6,5] analog of julolidine aldehyde, can be prepared by: (1) the reaction of indoline with 3-chloropropionyl chloride to form 1-(3-chloropropionyl)indoline, (2) ring closure with aluminum chloride, (3) reduction of the amide to lilolidine (4H-pyrrolo[3,2,1-i,j]quinoline, 1,2,5,6-tetrahydro-) with lithium aluminum hydride, and (4) formulation as described above. The synthesis of lilolidine by steps 1–3 is described in Example 3. The synthesis of lilolidine has also been described by G. Barger and E. Dyer, *J. Am. Chem. Soc.*, 60, 2414–2416, 1938.

The advantageous properties of the compositions and processes of this invention can be observed by reference to the following examples.

EXAMPLES

| GLOSSARY | |
|---|---|
| BHT | Butylated hydroxytoluene; 2.6-Di-tert-butyl-4-methylphenol; CAS 128-37-0 |
| o-Cl-HABI | 1,1,-Biimidazole, 2,2,-bis[o-chlorophenyl]-4,4',5,5'-tetraphenyl-; CAS 1707-68-2 |
| DBC | Cyclopentanone, 2,5-bis-[4-(diethylamino)-2-methylphenyl]methylene]-; CAS |
| DEAW | Cyclopentanone, 2,5-bis[4-(diethylamino)phenyl]methylene]-; CAS 38394-53-5 |
| DMJDI | 1H-Inden-1-one, 2,3-dihydro-5,6-dimethoxy-2-[(2,3,6,7-tetrahydro-1H,5H-benzo[i,j]-quinolizin-9-yl)methylene]-; CAS 80867-05-6 |
| FC-430 | Fluorad ® FC 430, liquid nonionic surfactant; 3M Company |
| 9-JA | 9-Julolidine carboxaldehyde; 9-Carboxaldehyde, 2,3,6,7-tetrahydro-1H,5H-benzo[i,j]quinolizine; CAS 33985-71-6 |
| JAW | Cyclopentanone, 2,5-bis[(2,3,6,7-tetrahydro-1H,5H-benzo[i,j]quinolizin-9-yl)methylene]- |
| LLD | Lilolidine; 4H-Pyrrolo[3,2,1-i,j]quinoline, 1,2,5,6-tetrahydro- |
| MMT | 4-Methyl-4H-1,2,4-triazole-3thiol; CAS 24854-43-1 |
| NVC | N-Vinylcarbazole; 9-Vinylcarbazole; CAS 1484-13-5 |
| POEA | 2-Phenoxyethyl acrylate; CAS 48145-04-6 |
| Polyox ® WSRN-3000 | Polyethylene oxide MW 400,000 |
| TMPEOTA | Triacrylate ester of ethoxylated trimethylolpropane; CAS 28961-43-5 |
| TMPTA | Trimethylolpropane triacrylate; CAS 15625-89-5 |
| Vinac ® B-100 | Polyvinyl acetate, Air Products, M.W. 500,000; CAS 9003-20-7 |

EXAMPLE 1

Synthesis of JAW JAW is synthesized by the base catalyzed condensation of 9-JA with cyclopentanone. In 225 mL of methanol is dissolved 11.4 g (0.135M) of cyclopentanone, 55.0 g (0.273M) of 9-JA, and 2.8 g (0.07M) of sodium methoxide. The reaction mixture, heated at reflux, quickly turns dark red and red solid begins to separate. After 7.5 h of heating at reflux, the reaction mixture is allowed to cool to room temperature. After standing for about 40 h, the reaction mixture is cooled in an ice bath. The resulting red precipitate is filtered off and washed with cold methanol. Yield: 55.0 g (89%) of red crystals mp 268° C.–278° C. with decomposition. $\lambda_{max(methylene\ chloride)} = 496$ nm ($\epsilon = 62,000$).

EXAMPLE 2

Synthesis of 9-Julolidine Carboxaldehyde

9-JA is synthesized by the formulation julolidine with phosphorus oxychloride in N,N-dimethyl formamide by a procedure similar to that described for the formulation of N,N-dimethylaniline (*Organic Synthesis*, Coll. Vol. 4, Wiley, New York, 1963, pp 331–333). N,N-Dimethyl formamide (45 mL) is added to a round bottom flask fitted with a magnetic stirrer, pressure equalizing dropping funnel, and a Claisen head whose sidearm was fitted with a drying tube. The flask is flushed with dry nitrogen and then cooled in a dry ice/isopropyl alcohol bath. Phosphorus oxychloride (16 mL, about 26.3 g) is added. After 10 min, 19 g of julolidine is added dropwise with stirring. The reaction mixture is stirred for 15 min after addition of the julolidine is complete, heated on a steam bath for 2 hr, and poured into a slurry of about 400 mL of crushed ice and water. The resulting solution is carefully neutralized by the addition of 150 g of sodium acetate in 250 mL of water. The precipitated aldehyde is collected by filtration, and the filtrate is kept at 0° C. overnight. The additional precipitate thus formed is collected and combined with the first crop. The combined precipitates are treated with activated charcoal (Darco ® G-60) and recrystallized from ethanol/water to give 21.2 g (96%) of 9-JA as light yellow needles, mp 81° C.–82° C. [lit. 83° C., *J. Org. Chem.*, 17, 1281 (1952)].

EXAMPLE 3

Synthesis of Lilolidine

LLD is synthesized from indoline (CAS 496-15-1) by (1) reaction with 3-chloropropionyl chloride to form 1-(3-chloro-propionyl)indoline, (2) ring closure of the resulting 1-(3-chloropropionyl)indoline with aluminum chloride, (3) reduction of the ring closed amide to LLD with lithium aluminum hydride.

3-Chloropropionyl chloride (100 g) is added dropwise with stirring to 89.5 g of indoline in 100 mL of dry acetone. After 10 min, the reaction mixture is cooled to 5° C. and 60 mL of pyridine is added. After stirring for 0.5 hr, the reaction mixture is poured into a solution of 50 mL of concentrated hydrochloric acid in 1 L of water. The resulting precipitate is filtered, washed with about 3 L of water, dissolved in 1.6 L of hot ethanol, and treated with charcoal to produce a mixture which is filtered while hot. Water (about 1.6 L) is added to the filtrate. Buff needles of 1-(3-chloropropionyl)indoline (79.7 g, 51%) precipitate on standing (mp 91° C.–92° C.)

A mixture of 69.5 g of 1-(3-chloropropionyl)-indoline and 46.7 g of aluminum chloride in a 500 mL round bottom flask is heated at 170° C. for 2.5 hr. After the reaction mixture has cooled to room temperature, 50 mL of 1 N hydrochloric acid followed by 100 mL of water is carefully added. The product is extracted with two 300 mL portions of methylene chloride. The resulting solution is dried over magnesium sulfate, treated with charcoal, passed through a column of 0.5 lb of alumina, and evaporated to yield 50.4 g (88%) of the tricyclic amide (mp 108° C.-109° C.).

To a solution of 50 g of tricyclic amide in 3 L of dry diethyl ether is added 25 g of lithium aluminum hydride in 0.5 L of dry diethyl ether. After the reaction mixture is stirred at room temperature for 4 hr, 55 mL of water saturated sodium chloride solution is added over 1 hr, and the solution stirred for an additional 3 hr. The reaction mixture is filtered, and the ether evaporated to produce an oil which is vacuum distilled using a water aspirator. Yield 39.4 g (86%) (bp about 137° C.-147° C. at about 20 mmhg) [literature 140° C. at 12 mmhg, (G. Barger and E. Dyer, *J. Am. Chem. Soc.*, 60, 2414-2416, 1938)].

COMPARATIVE EXAMPLES A-C AND EXAMPLE 4

Prior art compounds DBC, DEAW, and DMJDI were prepared and their absorption spectra, determined in methylene chloride, compared with that of JAW. The location of the absorption maximum ($\lambda_{max}$) and the extinction coefficients ($\epsilon$) at the absorption maximum, at 488 nm (one of the lines of the argon ion laser) and at 532 nm (the wavelength of the frequency doubled neodymium:YAG laser) are given in the table. The absorption maximum for JAW occurs at a longer wavelength than does that of any of the prior art compounds. JAW also absorbs much more strongly than DMJDI at both the 488 and 532 nm and much more strongly than either DBC or DEAW at 532 nm.

| Compound | $\lambda_{max}$ | $\epsilon_{max}$ | $\epsilon_{488}$ | $\epsilon_{532}$ |
|---|---|---|---|---|
| DBC | 481 nm | 59,200 | 57,400 | 7,200 |
| DEAW | 477 nm | 74,000 | 65,200 | 3,100 |
| DMJDI | 442 nm | 37,400 | 6,900 | 0 |
| JAW | 496 nm | 59,600 | 57,600 | 22,300 |

EXAMPLE 5

This example illustrates that the sensitizers of this invention are useful in holographic photopolymer compositions. Further it illustrates that the sensitizers of this invention can be used to sensitize photopolymerizable compositions to the 568 nm output of a krypton-ion laser.

A composition containing 16.21 g of Vinac ® B-100, 6.0 g POEA, 1.5 g NVC, 0.75 g o-Cl HABI, 0.50 g MMT, 0.025 g FC-430, 0.0025 g BHT, 0.015 g JAW, 6.0 g 2-butanone, and 69.0 g methylene chloride was coated onto a 0.004 inch thick clear film support of polyethylene terephthlate using a Talboy ® coater equipped with an 0.008 inch doctor knife, 12 foot drier set at 40° C.-50° C., and a laminator station. The coating speed was 8 ft/min. A cover sheet of 0.0009 inch polyethylene terephthlate was laminated to the coating as it came out of the drier. Cover sheet and film support were left in place during all subsequent handling, exposure, and processing operations.

A 4×5 inch sample of this material, sandwiched between a glass plate and an aluminized front-surface mirror, was exposed to a collimated 568 nm krypton-ion laser beam orientated perpendicular to the film plane and passing, in order, through the glass plate, film support, coating, and cover sheet and then, after reflecting off the mirror, back through back the cover sheet, coating, film support, and glass plate. The beam had a diameter of about 1.4 cm and an intensity of about 15 mW/cm². Exposure time was 20 sec corresponding to 300 mJ/cm² total exposure.

The imaged sample containing the holographic mirror was overall exposed to ultraviolet and visible radiation using a Douthitt type DCOP-X exposure unit (Douthitt Corporation, Detroit, MI) fitted with a photopolymer mercury arc lamp (Theimer-Strahler #5027). The sample was then heated to 100° C. for 15 min in a convection oven. The holographic mirror was analyzed by recording its transmission spectrum on a Hitachi Perkin-Elmer model 330 spectrophotometer. The maximum reflection efficiency was 87% at 565 nm.

EXAMPLE 6

Unexpected improvements of resist characteristics are demonstrated for a formulation containing a composition of this invention JAW. Two formulations are prepared having the same components except that formulation A contains the sensitizer JAW which has an absorption maximum at 496 nm and control formulation B contains the prior art sensitizer DMJDI Which has an absorption maximum at 442 nm. The components of the coating formulation are:

| COMPONENT | GRAMS |
|---|---|
| Methanol | 50.00 |
| Methylene chloride | 600.00 |
| Polyox ®, WSRN-3000 | 1.47 |
| TMPTA | 21.00 |
| TMPEOTA | 73.50 |
| Poly(methyl methacrylate/ethyl acrylate/ methacrylic acid) (51/29/20), Wt. Ave. M.W. 40,000-47,000, Tg 80° C., Acid No. 131 | 208.00 |
| Benzophenone | 28.00 |
| o-Cl-HABI | 14.00 |
| Leuco Crystal Violet | 1.05 |
| N-Phenyl glycine | 2.60 |
| Sensitizer (JAW or DMJDI) | 0.95 |

Each coating formulation is conventionally coated onto a 0.001 in thick polyethylene terephthalate film support and dried to give a dry coated layer thickness of about 0.0015 in. A 0.001 in polyethylene coversheet is laminated to the uncovered surface of each coated layer to protect it during storage and handling.

After the protective coversheet is removed, each coated layer is laminated to a copper clad circuit board substrate which was scrubbed with an abrasive brush, using a Riston ® hot roll laminator. Each laminated layer was imagewise exposed under vacuum to radiation having wavelengths greater than 460 nm using the filtered output of a Riston ® PC Printer. In this exposure procedure, an Air Force Resolution Target phototool and a 0.001 in thick sheet of Kapton ® polyimide film was placed over the polyethylene terephthalate support of the laminated layer in the vacuum frame of the PC Printer and irradiated to give 25 mJ/cm² exposure at the polyimide film surface. The polyimide sheet is substantially opaque to radiation having wavelengths less than 460 nm, i.e., the sheet has an optical density of 1.6 at 460 nm, an optical density of 2 at 450 nm and higher optical densities at shorter wavelengths.

After exposure, the polyethylene terephthalate support film is removed from the laminate and the unexposed portions of the photopolymer layer are removed with a 1% by weight aqueous solution of sodium carbonate monohydrate at 85° F. using a Chemcut ® 547 processing system at a transport rate of about 73 in/min.

The uncovered copper laminate surface, protected by the developed photoresist, is then conventionally electroplated: first with 0.0009 inches of copper, then with 0.0005 inches of nickel and finally with 0.0001 inches of gold. Copper and nickel plating are carried out at a current density of 30 amp/ft$^2$ using a conventional acidic hi thro copper solution and an acidic nickel sulfamate solution respectively. Gold plating is carried out at a current density of 10 amp/ft$^2$ using an Orosene ® 999 plating bath. During gold plating considerable bubbling, due to the evolution of hydrogen gas, takes place at the exposed circuit lines being plated. For control resist samples containing DMJDI, the resist blistered and raised from the copper surface at circuit line edges. In contrast, the resist sample containing JAW remained free of any such defects.

The photopolymerized resist is then conventionally striped from the plated laminate using 1.5% KOH at 130° F. in an ASI Stripping Unit. The uncovered copper, not protected by gold plating, is etched away to form a gold plated conductive line negative image of the original target phototool. The sample prepared with the DMJDI resist had lines with jagged edges and connections between closely spaced lines indicating that printed circuit lines which are spaced 0.003 inches apart or closer would contain electrical shorts. In contrast, The sample prepared with JAW is free of such defects down to line spacing of 0.002 inches or shorter indicating utility in preparing more closely packed printed circuits.

EXAMPLE 7

This example demonstrates that an unexpected increase in the thermal stability of photopolymerizable compositions was observed when prior art sensitizer DMJDI was replaced with JAW, a sensitizer of this invention.

The stock coating solution indicated below was prepared at about 35% solids in 95:5 dichloromethane/methanol.

| COMPONENT | PERCENT BY WEIGHT |
|---|---|
| Polyox ® WSRN-3000 | 0.42 |
| TMPTA | 6.0 |
| TMPEOTA | 21.0 |
| Poly(methyl methacrylate/ethyl acrylate/methacrylic acid) (51/29/20), Wt. Ave. M.W. 40,000–47,000, Tg 80° C., Acid No. 131 | 47.4 |
| Binder A[a] | 12.0 |
| Benzophenone | 8.0 |
| o-Cl-HABI | 4.0 |
| Leuco Crystal Violet | 0.30 |

| COMPONENT | PERCENT BY WEIGHT |
|---|---|
| N-Phenyl glycine | 0.74 |

[a] Binder A is prepared by the following procedure. An emulsion polymerization apparatus consisting of a 5 L, 4 necked flask equipped with a mechanical stirrer, a 1 L addition funnel, thermometer, nitrogen inlet, water cooled reflux condenser and a heating mantle is charged with 3,360 g of deionized water and 20 g of a 30% aqueous solution of sodium lauryl sulfonate and heated to 80° C. under a nitrogen atmosphere. At that temperature 25% of a mixture of 420 g of methyl methacrylate, 240 g ethyl acrylate, 165 g methacrylic acid, and 16 allyl methacrylate is added in one shot, immediately followed by 10 mL of 5% aqueous potassium persulfate and 10 mL of 7% aqueous potassium phosphate. The remainder of the monomer mixture is added over a period of 90 min while the temperature is maintained at 80–88° C. Then the reaction is heated at 80–85° C. for an additional 2 hr. The reaction mixture is cooled to room temperature and the product coagulated with methanol. The resulting slurry is filtered, washed twice with water and sucked dry. The resulting fine powder is dried in an oven at 100° C. for 4 hr.

The stock coating solution was divided into portions and sensitizer added as indicated in the following table. The resulting coating solutions were board coated with a doctor knife and air dried to give coatings about 1.5 mil (38 microns) thick. A small portion of each coating was removed and the polymerization temperature determined with a Du Pont 1090 DSC. The maximum of the heat flow versus temperature curve was taken as the polymerization temperature.

| SENSITIZER | POLYMERIZATION TEMPERATURE |
|---|---|
| 0.28% DMJDI | 113° C. |
| 0.05% JAW | 114° C. |
| 0.10% JAW | 118° C. |
| 0.20% JAW | 122° C. |
| 0.28% JAW | 125° C. |

EXAMPLE 8

This example demonstrates that an unexpected increase in both speed and resolution was observed when prior art sensitizer DMJDI was replaced with JAW, a sensitizer of this invention.

Two of the coatings prepared in Example 7 were laminated to a copper clad circuit board substrate which was scrubbed with an abrasive brush, using a Riston ® hot roll laminator at about 210° F. (99° C.) at a speed of 5 ft/min (152 cm/min). Each laminated layer was imagewise exposed under vacuum to radiation having wavelengths greater than about 460 nm using the filtered output of a Riston ® PC Printer. In this exposure procedure, a Stouffer Resolution Chart and a 1 mil (25 micron) thick sheet of Kapton ® polyimide film was placed over the polyethylene terephthalate support of the laminated layer in the vacuum frame of the PC Printer and irradiated to give exposures at the polyimide film surface indicated in the following table. The polyimide sheet is substantially opaque to radiation having wavelengths less than 460 nm, i.e., the sheet has an optical density of 1.6 at 460 nm, an optical density of 2 at 450 nm and higher optical densities at shorter wavelengths.

After exposure, the unexposed portions of the photopolymer layer were removed with a 1% by weight aqueous solution of sodium carbonate monohydrate at 85° F. (29° C.) using a Chemcut ® 547 processing system at a transport rate of about 73 in/min (185 cm/min).

The uncovered copper laminate surface, protected by the developed photoresist, was then conventionally electroplated: first with about 0.9 mil (23.0 micron) of copper, then with about 0.5 mil (12.7 micron) of nickel and finally with about 0.1 mil (2.5 micron) of gold. Copper and nickel plating were carried out at a current density of 30 amp/ft² using a conventional acidic hi thro copper solution and an acidic nickel sulfamate solution respectively. Gold plating was carried out at a current density of 10 amp/ft² using an Orosene ® 999 plating bath.

The photopolymerized resist was then conventionally striped from the plated laminate using 1.5% KOH at 130° F. (54° C.) in an ASI Stripping Unit. The uncovered copper, not protected by gold plating, was etched away to form a gold plated conductive line negative image of the original target phototool. Speed (number of sixth root of 2 steps held) and resolution (width of the narrowest line held) are given in the following table. Resolution was measured both after etching but before plating and after plating.

| SENSITIZER | EXPOSURE[a] | $2^{1/6}$ STEPS | RESOLUTION[b] Etching | RESOLUTION[b] Plating |
|---|---|---|---|---|
| 0.28% DMJDI | 30 | 16 | 1.9 | 2.9 |
| 0.28% DMJDI | 60 | 22 | 2.4 | 6.0 |
| 0.28% JAW | 30 | 19 | 1.5 | 1.6 |
| 0.28% JAW | 60 | 25 | 2.0 | 2.4 |

[a] mJ/cm²
[b] width of finest lines held in mils.

What is claimed is:

1. A photosensitive composition comprising:
   (a) a compound of the formula:

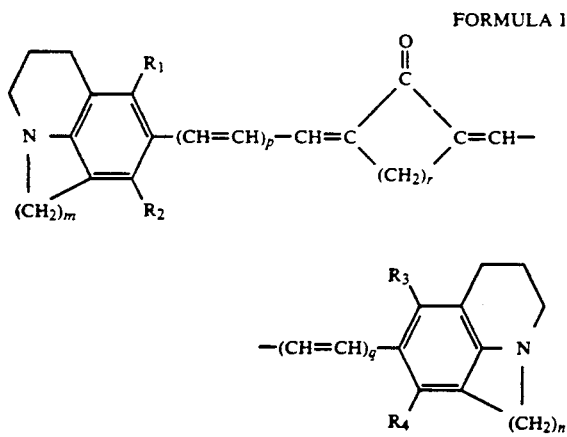

FORMULA 1 wherein p and q independently are 0 or 1 and r, m and n independently are 2 or 3; and $R_1$, $R_2$, $R_3$ and $R_4$, independently are selected from the group consisting essentially of hydrogen and alkyl having 1 to 4 carbon atoms or alkoxy having 1 to 4 carbon atoms.
   (b) an ethylenically unsaturated compound capable of free radical generated addition polymerization,
   (c) a free radical generating initiation system activated by actinic radiation.

2. Composition of claim 1 present as a liquid.
3. The composition of claim 1 present as a dry film.
4. The composition of claim 1 wherein p and q are 0, m and n are 3, r is 2 and $R_1$, $R_2$, $R_3$ and $R_4$ are hydrogen.
5. The composition of claim 1 wherein said initiation system comprises a HABI and a chain transfer
6. A photosensitive composition comprising:
   (a) a compound of the formula:

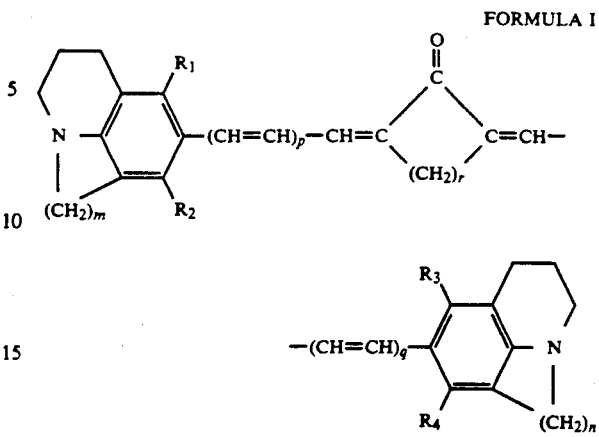

FORMULA I wherein p and q independently are 0 or 1 and r, m and n independently are 2 or 3; and $R_1$, $R_2$, $R_3$ and $R_4$, independently are selected from the group consisting of hydrogen and alkyl having 1 to 4 carbon atoms or alkoxy having 1 to 4 carbon atoms,
   (b) an ethylenically unsaturated compound capable of free radical generated addition polymerization,
   (c) a free radical generating initiation, system activated by actinic radiation,
   (d) a polymeric material.

7. The composition of claim 6 wherein p and q are 0, m and n are 3, r is 2 and $R_1$, $R_2$, $R_3$ and $R_4$ are hydrogen.

8. A process for forming a photoresist on a substrate comprising the steps of:
   (a) applying to the substrate a photosensitive composition,
   (b) imagewise exposing the composition to actinic radiation,
   (c) removing unexposed areas of the composition to form resist areas,
   (d) permanently modifying areas of the substrate which are unprotected by the resist areas by etching the substrate or by depositing a material onto the substrate,
   wherein the photosensitive composition comprises:
   (i) a compound of the formula:

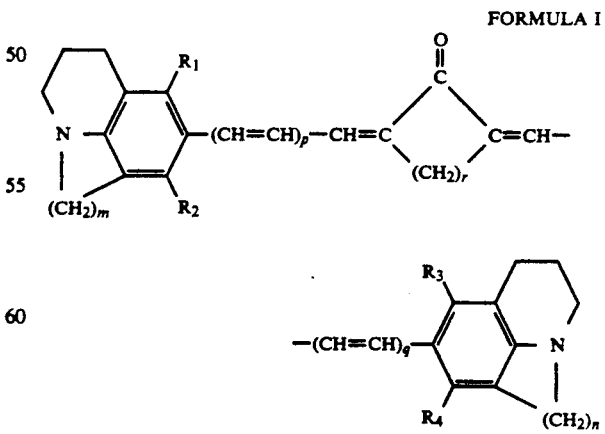

FORMULA I wherein p and q independently are 0 or 1 and r, m and n independently are 2 or 3; and $R_1$, $R_2$, $R_3$ and $R_4$, independently are selected from the group consisting of hydrogen and alkyl having 1 to 4 carbon atoms or alkoxy having 1 to 4 carbon atoms, (ii) an ethylenically unsaturated compound capable of free radical generated addition polymerization, (iii) a free radical generating initiation system activated by actinic radiation.

9. The process of claim 8 wherein the resist areas are removed from the substrate after step (d).

10. The process of claim 8 wherein p and q are 0, m and n are 3, r is 2 and $R_1$, $R_2$, $R_3$ and $R_4$ are hydrogen.

11. A single step process for forming a lightstable hologram which comprises exposing to modulated actinic radiation bearing holographic information a photopolymerizable layer comprising:

(a) a compound of the formula:

FORMULA I

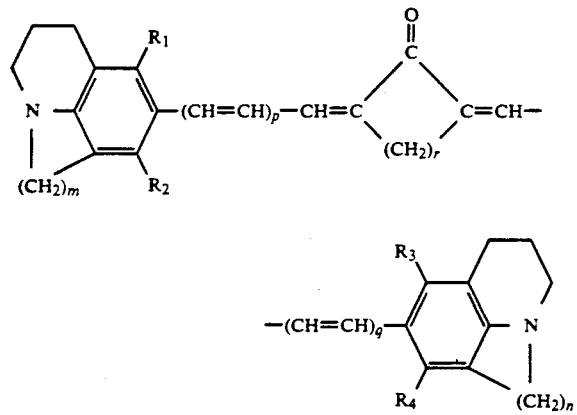

wherein p and q independently are 0 or 1 and r, m and n independently are 2 or 3; and $R_1$, $R_2$, $R_3$ and $R_4$, independently are selected from the group consisting of hydrogen and alkyl having 1 to 4 carbon atoms or alkoxy having 1 to 4 carbon atoms, (b) a solvent soluble, thermoplastic polymeric binder, (c) at least one liquid ethylenically unsaturated monomer capable of addition polymerization and having a boiling point above 100° C., and (d) a free radical generating system activatable by actinic radiation.

12. The process of claim 11 wherein the modulated actinic radiation of a reference beam and an object beam enter on the same side of the photopolymerizable layer to form a transmission hologram.

13. The process of claim 11 wherein the modulated actinic radiation of a reference beam and an object beam enter on the opposite sides of the photopolymerizable layer to form a reflection hologram.

14. The process of claim 13 wherein the coherent radiation of a reference beam which is transmitted through the photopolymerizable layer to illuminate an object and generates an object beam by reflection back through the photopolymerizable layer.

15. The process of claim 11 wherein said free radical generating system activatable by actinic radiation comprises a HABI and a chain transfer agent.

16. The process of claim 15 wherein either said binder or said ethylenically unsaturated monomer contains a substituent selected from the group consisting of phenyl, phenoxy, naphthyl, naphthyloxy, heteroaromatic containing up to three aromatic rings, chlorine, bromine, and mixtures thereof, and the other constituent is substantially free of said substituent.

17. The process of claim 15 wherein said ethylenically unsaturated monomer contains a substituent selected from the group consisting of phenyl, phenoxy, naphthyl, naphthyloxy, heteroaromatic containing up to three aromatic rings, chlorine, bromine, and mixtures thereof, and the binder is substantially free of said substituent.

18. The process of claim 17 in which a solid ethylenically unsaturated monomer is also present.

19. The process of claim 18 wherein said solid ethylenically unsaturated monomer is N-vinyl carbazole.

20. The process of claim 19 wherein p and q are 0, m and n are 3, r is 2, and $R_1$, $R_2$, $R_3$ and $R_4$ are hydrogen.

* * * * *